United States Patent [19]

Silver

[11] Patent Number: 5,121,641

[45] Date of Patent: * Jun. 16, 1992

[54] BEET TARE-TAKING APPARATUS

[76] Inventor: Joseph M. Silver, 1568 28th Street, Ogden, Utah 84401

[*] Notice: The portion of the term of this patent subsequent to Oct. 29, 2008 has been disclaimed.

[21] Appl. No.: 531,167

[22] Filed: May 31, 1990

Related U.S. Application Data

[63] Continuation-in-part of Ser. No. 513,085, Apr. 23, 1990.

[51] Int. Cl.⁵ ............................................. G01N 1/20
[52] U.S. Cl. ................................. 73/863.52; 73/864.32
[58] Field of Search ........... 73/863.52, 863.53, 864.31, 73/864.32, 864.51

[56] References Cited

U.S. PATENT DOCUMENTS

| | | | |
|---|---|---|---|
| 2,600,329 | 6/1952 | Romine et al. | 73/863.52 |
| 2,650,498 | 9/1953 | Armer | 73/863.52 |
| 3,358,512 | 12/1967 | Silver et al. | 73/863.53 |
| 3,373,615 | 3/1968 | Silver et al. | 73/863.53 |
| 3,687,362 | 8/1972 | Del Rosso | 209/593 X |
| 4,122,721 | 10/1978 | Zubricki | 73/864.51 X |
| 4,558,602 | 12/1985 | Redding | 73/864.32 X |

Primary Examiner—Tom Noland
Attorney, Agent, or Firm—A. Ray Osburn

[57] ABSTRACT

A beet tare-taking mechanism and associated sample bucket, wherein the bucket travels in a long narrow elliptic path requiring minimum clearance. A direct drive gear powers a central arm at the end of which is journaled a tare bucket arm carrying the bucket at its outermost end. The tare bucket is geared to rotate with respect to the central arm as it rotates about the central shaft, alternately folding across the mechanism and extending directly outward from it, causing the bucket to travel in the aforementioned elliptic path.

13 Claims, 8 Drawing Sheets

BEET TARE-TAKING APPARATUS

RELATED APPLICATION

This application is a continuation in part application based on co-pending application Ser. No. 07/513,085, filed Apr. 23, 1990; Inventor Joseph Moyle Silver, entitled BEET TARE-TAKING APPARATUS.

FIELD

The field of the present invention is tare sampling apparatus and more particularly such apparatus adapted for sampling a moving stream of beets.

STATE OF THE ART

The large scale growing, harvesting and processing of sugar beets prompted the early design and manufacture of automatic beet handling apparatus called pilers wherein the beets were dumped or otherwise transferred from the harvesting wagons, trucks or the like onto a system of conveyor belts so as to ultimately be stored in large piles at the processing plant or the rail loading sidings. The beets typically were first elevated then cascaded through a screening device to dislodge the bulk or adhering soil and other foreign material. However, the screened beets still carry significant amounts of foreign materials which must be quantified before reimbursement of the grower. Also, the sugar content of the beets, after divestment of adhered soil, required similar measurement. Accordingly, various tare sample taking devices have been conceived and developed. From the screening portion of the piler, the beets typically free fall a short distance into another elevating conveyor, generally controlled by a gantry boom on the piler, for transport up onto the storage pile. Initially, the sample bucket was manually inserted into the stream of falling beets to be filled and withdrawn. However, it was not long until various mechanical devices were developed for this purpose. Perhaps the simplest of these was a bucket held on the end of a pivoting arm which was rotated by crank means to insert the bucket into and withdraw it from the stream. Powered devices basically inserting the bucket through swinging it in complete or partial circles became common. Sometimes these devices also included provisions for elevating the sample to a higher level where the sample was transferred to a tare house actually built as part of the piler. More recently, this utilization of the tare house has become less prevalent, the beets being transported as necessary to the closest testing laboratory, wherein both the foreign material and the sugar content is determined. Examples of powered beet sampling machines are found in U.S. Pat. No. 2,650,498 to Armer (the tare bucket swinging through a near vertical plane briefly into the edge of the stream of beets and then being rotated away and elevated by a complicated combination of gearing and linkages), U.S. Pat. No. 2,600,329 to Romine et al (the tare bucket pivoted through approximately 180° so as to enter the beet stream and reversely withdraw therefrom), U.S. Pat. No. 3,358,512 to J. W. Silver et al (the tare bucket powered to make full circular swings in a horizontal plane to pass through a portion of the stream of beets) and U.S. Pat. No. 3,373,615 to J. M. Silver et al (tare bucket path requires little clearance for filling, but the bucket swings wide to reach dumping position). Almost all of these prior art devices share the disadvantage of requiring considerable horizontal space in which to accommodate the moving bucket and its support arm. Accordingly, the bucket in most of these apparatus may not fully penetrate or traverse the stream of beets, so that the sample taken may not be accurately representative. This is especially true in more advanced piler designs, which often involve a larger and wider stream of beets. Therefore, there remains a need for a beet tare sample taking apparatus wherein the bucket moves continuously without reversal through the stream of beets, and wherein the installation space requirement is minimized.

BRIEF SUMMARY OF THE INVENTION

With the foregoing in mind, the present invention eliminates or substantially alleviates the shortcomings and disadvantages in prior art beet tare sampling devices, being such a device requiring minimum installation and operating space while providing continuous, unreversed movement of a sampling bucket into, through and out of the stream of beets. The required space is shaped for easy installation within the clearances provided by beet piler structures. The bucket travels horizontally through a long narrow elliptic path around a central propelling mechanism, being carried on the far end of a bucket arm which at its other end is journaled to rotate about the distal end of a central arm which in turn revolves about a fixed vertical axis at its other end. The bucket arm is made to rotate with respect to the central arm at twice the latter's rate of rotation, but in the opposite direction, so that the bucket arm, during each revolution of the central arm is successively twice folded parallel inwardly to and extended parallel outwardly from the rotating central arm, resulting in the aforesaid narrow elliptic path.

In more detail, a fixed support structure carries a fixed central gear coaxially with a vertical shaft driving the horizontal central arm, the latter in turn carrying at its distal end a vertical bucket arm shaft with an affixed coaxial gear and the horizontal bucket arm with the bucket at its far end. An idler gear is mounted on the central arm spanning between fixed central and bucket arm gears. Alternately, an endless drive chain may be utilized to connect the central and bucket arm gears. The connected gears cause the bucket arm shaft and arm with attached bucket to rotate about the vertical axis of the shaft at the distal end of the central arm as the latter is driven in a horizontal circular path centered upon the drive shaft. With the central to bucket arm gear ratio selected to be 2:1, each complete revolution of the central arm is accompanied by two complete revolutions of the bucket arm gear and shaft with respect to said arm. Since the bucket arm rotates oppositely to the central arm, it actually also rotates through only a single revolution with respect to the ground. During each quarter revolution of the central arm, the bucket arm turns through a half revolution with respect to the central arm and, if initially aligned inwardly therewith, rotates to a position extending directly outwardly therefrom. That is, during each revolution of the drive shaft, the bucket arm is successively positioned aligned parallel to the central arm inwardly toward the central gear, outwardly therefrom, then again inwardly and again outwardly. The path of the bucket at the free end of the bucket arm is similar to an oblong ellipse as long as approximately twice the sum of the lengths of the central end bucket arms, and as wide as twice the length of the central arm or the length of the bucket arm whichever is greater. This is minimizes required lateral clearance while providing extended bucket reach for collecting and depositing the sampled beets.

Preferably, an electric motor is suitably linked through sprocket gears and chain to power the tare-taker drive shaft. This provides predictable sampling bucket speed through the beet stream for accurate sampling, and the speed can be selected by choice of relative sprocket gear sizes. Preferably, the motor has a built-in solenoid brake or the like, so that the filled bucket may be easily stopped at the desired point in its path for unloading the sampled beets and foreign material.

In accordance with one aspect of the invention, the central arm may be driven by a direct drive gear fixed directly thereto, rather than through the aforementioned drive shaft. This embodiment preferably utilizes a large diameter central arm direct drive gear, so that the gear may be powered with motor means mounted upon convenient structure of the piler, for example. The direct drive gear may, at the option of the designer be powered by chain or pinion gear means.

Advantageously, the tare sampling bucket may be wholly or partially constructed of deformable elastic material such as highly flexible plastic. This is to obviate damage by encounters with chance obstructions in its path. such as errant beets, sticks and the like, as well as to enable the bucket to deform to get past permanent obstructions in some cases.

It is therefore the principal object of the invention to provide an improved beet tare sampling apparatus which can operate within the typically restricted clearances provided by beet piler structures, which nevertheless provides for predictable, selective sampling bucket speed through the stream of beets without reversal of path direction inside or outside of the beet stream.

BRIEF DESCRIPTION OF THE DRAWINGS

In the drawings, which represent the best modes presently contemplated for carrying out the invention.

DETAILED DESCRIPTION OF ILLUSTRATED EMBODIMENTS

Figure 1:
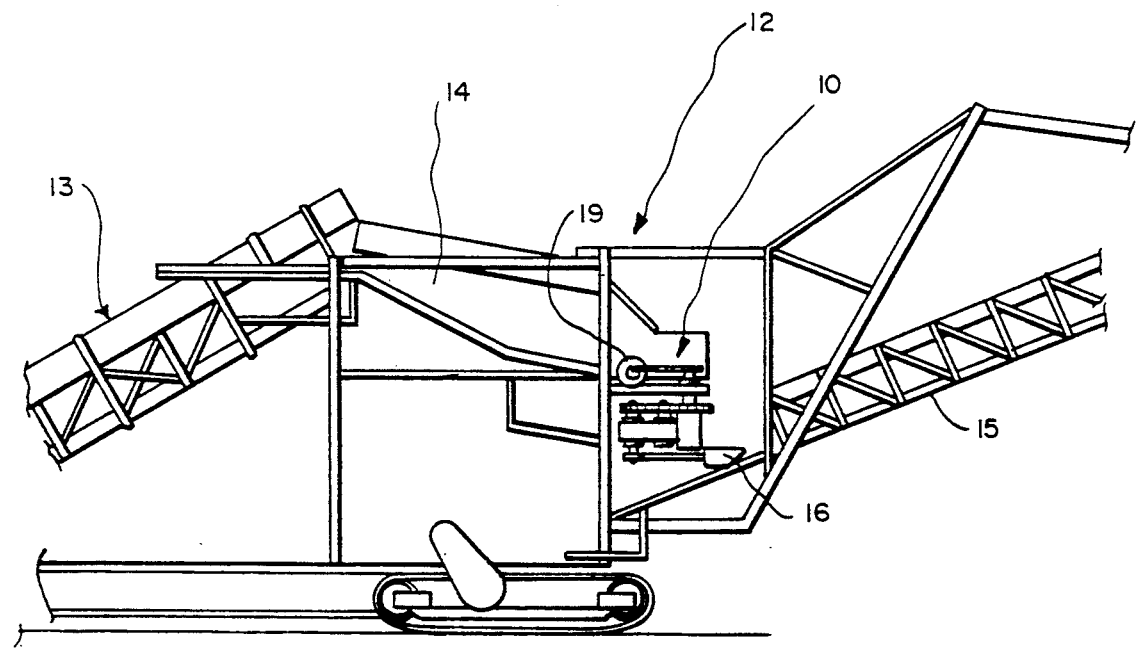
FIG. 1 is a reduced scale drawing showing a beet tare taking apparatus in accordance with the invention installed upon a beet piler, the latter fragmentally shown, FIG. 2 a schematic plan view showing the elliptic path of the tare bucket in and out of a stream of beets, intermediate positions of the bucket and central and bucket arms being indicated in dotted lines, drawn to a reduced scale, FIG. 3 a perspective view of the tare taker of FIG. 1, the mounting structure and debris shields omitted for clarity, drawn to a larger scale than FIG. 2, FIG. 4 a side elevation view of the beet tare taker of FIG. 1, partially cut away to show construction details, drawn to the approximate scale of FIG. 3, FIG. 5 a right side elevation view of the tare taker of FIG. 4, taken along line 5—5 thereof, drawn to the same scale, FIG. 6 a horizontal cross sectional view of the tare taking apparatus of FIG. 4, taken along line 6—6 thereof, the central arm however being rotated 90° from its position in FIG. 4, drawn to the same scale, FIG. 7 a plan view of a fragment of another embodiment in accordance with the invention, wherein the fixed and bucket arm gears are connected by an endless chain, drawn to the scale of FIG. 6, FIG. 8 a perspective view of a tare taking bucket constructed of flexible elastic material, drawn to approximately the scale of FIG. 2, FIG. 9 an elevation view of a fragment of the tare taker of FIG. 4, showing an alternative manual power means, drawn to the scale of FIG. 4.

A beet tare sample collection device, generally 10, is shown in FIG. 1 secured from a structural post 11 of a beet piler 12 fragmentally shown. Piler 12 has an upwardly inclined conveyor 13 through which beets dumped from trucks pass to a screen 14 to separate loose foreign material, and thence drop onto a gantry controlled conveyor 15 to be carried upward and dumped onto the beet storage pile. Tare sample taker 10 inserts a sample bucket 16 into the stream of beets falling from the screener 14 to the gantry conveyor 15.

Figure 3:
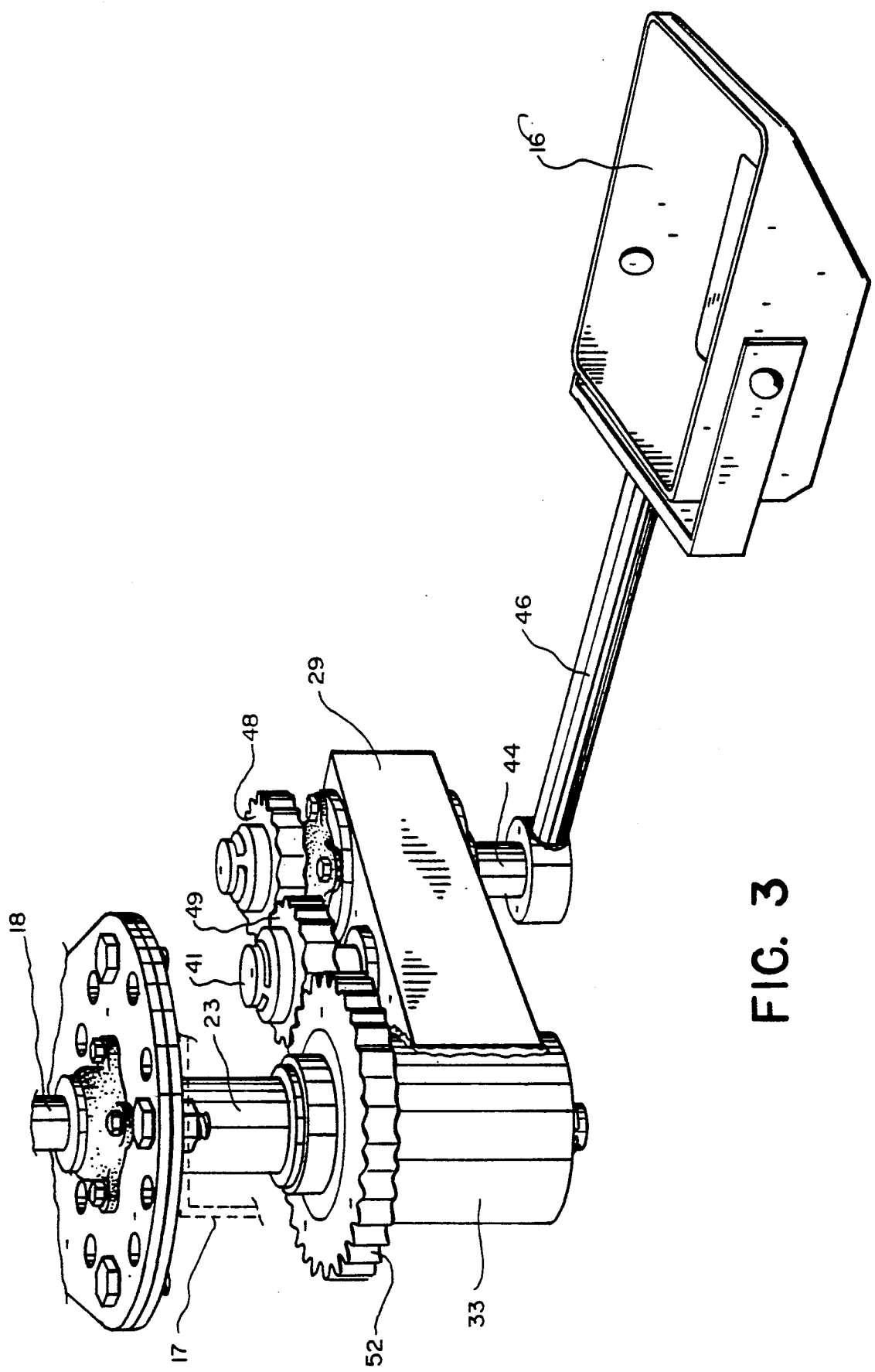
Figure 4:
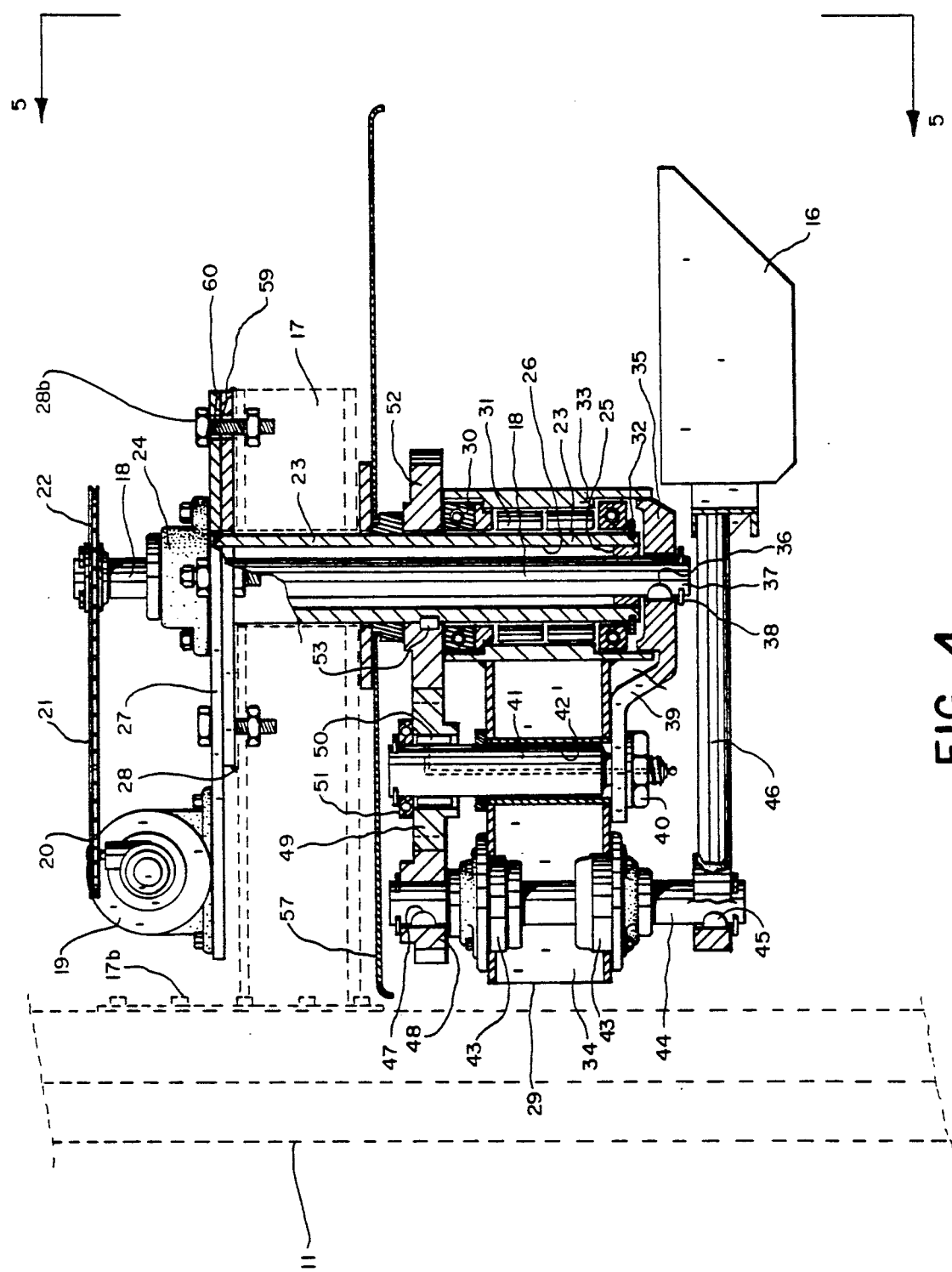
Figure 5:
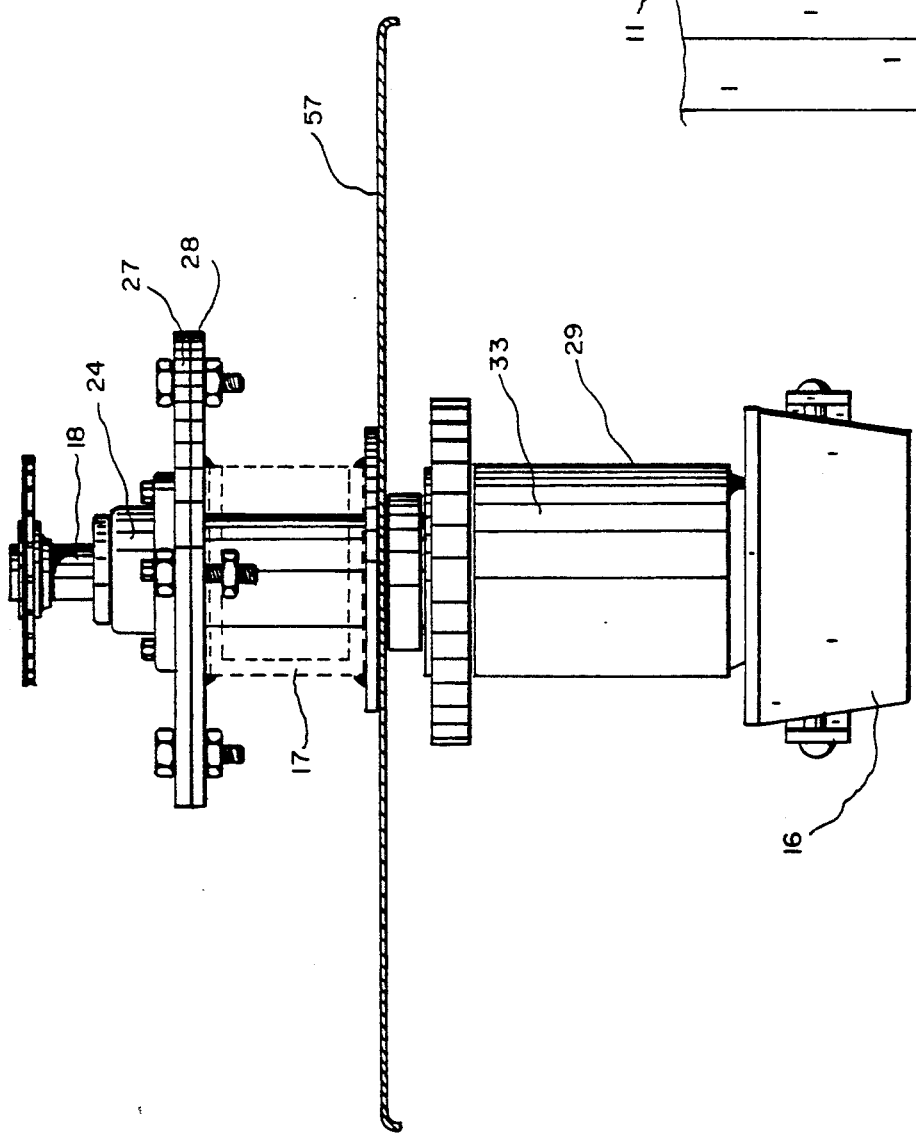

Tare sampling assembly 10 is secured to the post 11 as by a cantilevered structure 17. (FIGS. 3-5) A vertical shaft 18 drives the apparatus 10, powered by a brake equipped electric motor 19 with a worm gear driven sprocket 20, through chain 21 and drive shaft mounted sprocket 22. Drive shaft 18 is journaled into a drive shaft support tube 23, through an upper self-aligning gear 24 and a lower lubricated pilot bushing 25 respectively, the bushing 25 acting between drive shaft 18 and wall 26 of tube 23. A tube mounting plate 27 is welded to the top end of tube 23, and a matching plate 28 welded to support structure 17. Mounting bolts 28b connect plates 27 and 28, securing tube 23 in fixed position to structure 17, which in turn is rigidly secured to piler post 11 as by bolts 17b.

A central arm assembly 29 is journaled to rotate about tube 23, supported by thrust bearings 30 and shaft bearings 31, supported by a snap ring 32. Bearings 30 and 31 are contained within a cylindrical member 33. Central arm 29 comprises a horizontal extension 34 of steel box tubing secured as by welding to cylinder 33. A shaft encircling collar 35 is secured irrotatably by a key 36 upon lower end 37 of drive shaft 18 by a snap ring 38.

To collar 35 is secured a drive member 39 clamped to box tubing 34 by nut 40 on the lower end of an idler gear pinion 41 installed in a bore 42. Box tubing 34 is bored to accept near its outermost end a pair of aligned bearings 43. Journaled within the bearings 43 is a vertical shaft 44, to which is secured at its lowermost end a bucket arm 46 through a key 45, carrying sampling bucket 16 at its far end. At its uppermost end, secured by key 47, is a bucket arm gear 48.

Meshing with bucket arm gear 48 is an idler gear 49, supported rotatably about pinion 41 by thrust and shaft bearings 50 and 51 respectively. Idler gear 49 also meshes with central gear 52, the latter secured immovably through a key 53 to drive shaft encasing tube 23. A horizontal shielding plate 57 is desirably provided secured to tube 23 to preclude the deposit of foreign material downward onto the gears and other parts of sampling apparatus 10.

Figure 2:
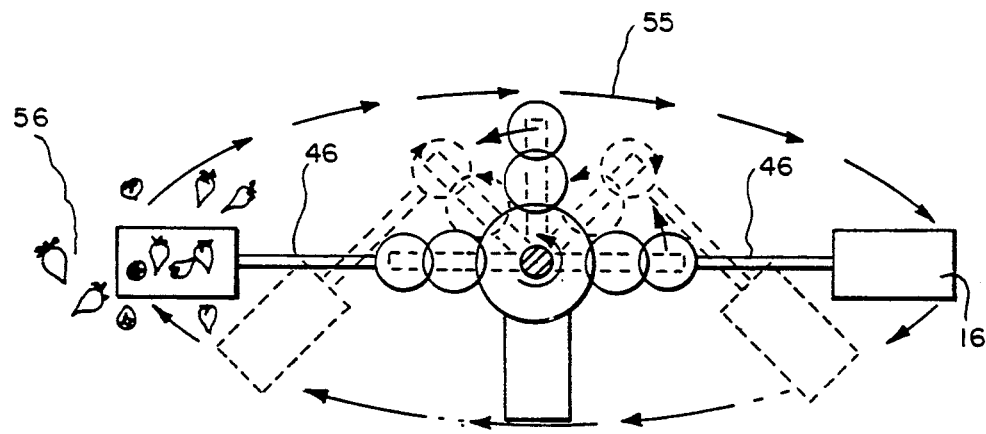
Figure 6:
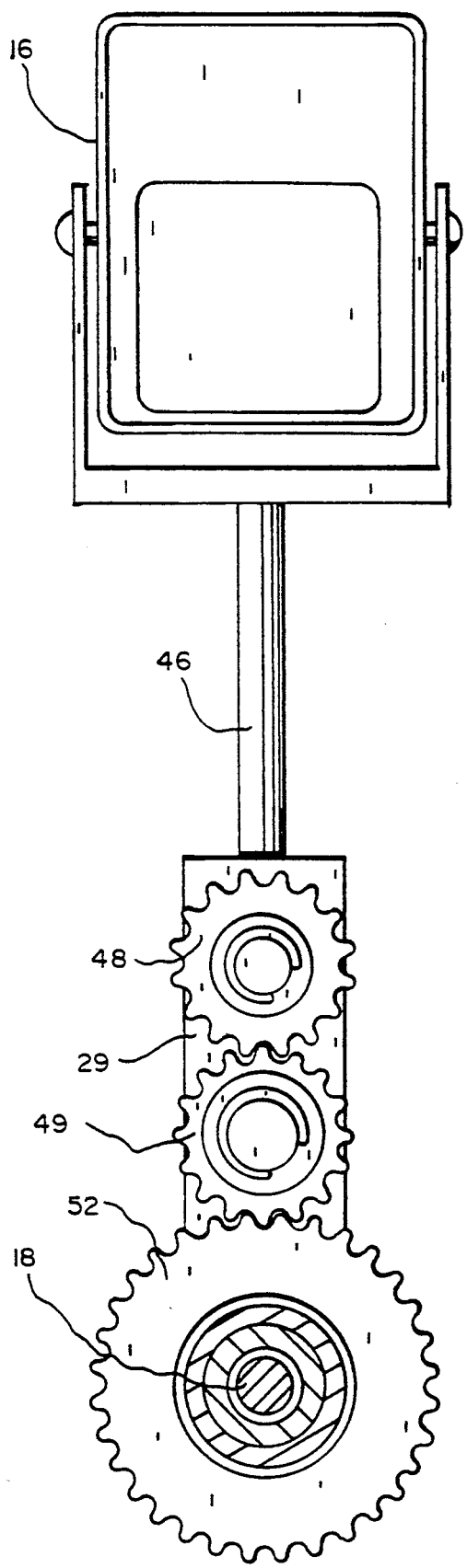

The gearing ratio between fixed central gear 52 and bucket arm gear 48 is selected at 2:1. When shaft 18 is rotated one full revolution about its vertical axis by motor 19, central arm 29 sweeps through a full circle 360°, during which bucket arm shaft 44 and attached bucket arm 46 are impelled (by fixed central gear 52 acting through idler gear 49 to bucket arm gear 48) to revolve oppositely two full circles with respect to the outstanding end 54 of central arm 29. Sampling bucket 16 is carried on the outstanding end 54 of bucket arm 40 along an ellipse-like path 55. (FIG. 2) Bucket 16 moves continuously without reversal along path 55 into and out of the falling stream of beets 56. When bucket 16 is extended fully toward the beets, bucket arm 46 is aligned outwardly from and parallel to central arm 29. Subsequently, bucket 16 and arm 46 rotate to a position inwardly parallel to central arm 29 when the latter extends directly across elliptic path 55, providing minimum required lateral clearance. (FIG. 4) Later the two arms 46 and 29 move so that the former extends outwardly from and parallel to the latter, with bucket 16 then at the outside end of ellipse 55. (FIG. 6) The sampling device 10 is then brought to a stop by switching off and braking motor 19, with bucket 16 then in position to be emptied of the beet sample, far removed from the beet stream, into a bag or other receptacle for subsequent tare measurements.

Preferably, the speed of bucket 16 is selected to be as required to sample beets from stream 56 without overfilling. If prematurely filled, additional loose tare material may be deposited into bucket 16 from impacting, but unretained, beets. Bucket speed is readily adjusted by selection of sprockets 20 and/or 22 to provide the ratio appropriate for desired bucket speed.

Path 55 combines extended bucket reach with minimum required lateral installation space. If, for example, the combined bucket arm and bucket lengths totals twice the length of the central arm the long axis of path 55 may be approximately two and one-half times the required lateral clearance, or more.

Support structure 17 is shaped and sized for best positioning of tare taker 10 vertically and horizontally on the structure of piler 12. Angular position of central arm 29 is adjusted by rotation of drive shaft 18 using motor 19. Subsequently, the angular position of bucket arm 46 with respect to the central arm is adjusted by selection of appropriate circularly arranged, angularly indexed, bores 59 in plate 27 to be engaged by mounting bolts 27b. The bores 59 may, for example, be at 30 degree intervals. A set of four matching bores 60 may be provided through plate 28 at 90 degree intervals. To permit a fine adjustment of plus or minus five degrees in bucket arm position, a companion pair of vernier bores 61 is provided 25 degrees to each side of each bore 60. Additional pairs vernier bores may be provided at other distances from the bores 60 if desired.

Figure 8:
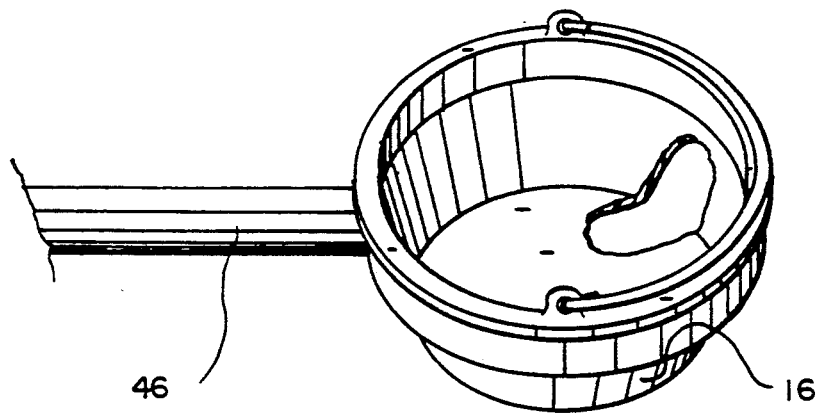

Desirably, bucket 16 may be constructed in whole or in part of flexible elastic material 58. (FIG. 8) The bucket may then be deformed to pass piler structure that may otherwise render the tare taker 10 inoperative. The chance of inadvertent damage to the bucket and other parts of tare taker 10 from encounters with misplaced beets, sticks, and the like along path 55 is also reduced.

Figure 9:
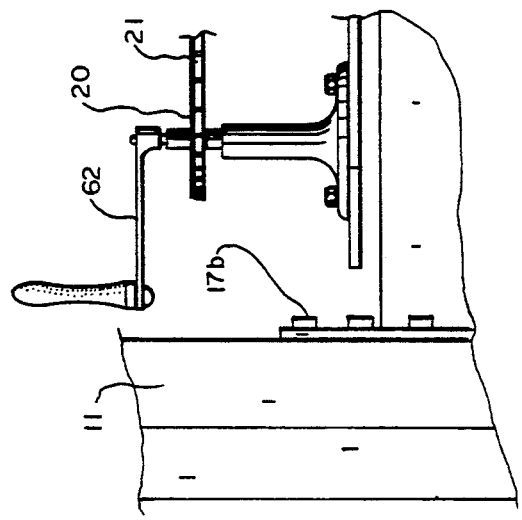
Figure 7:
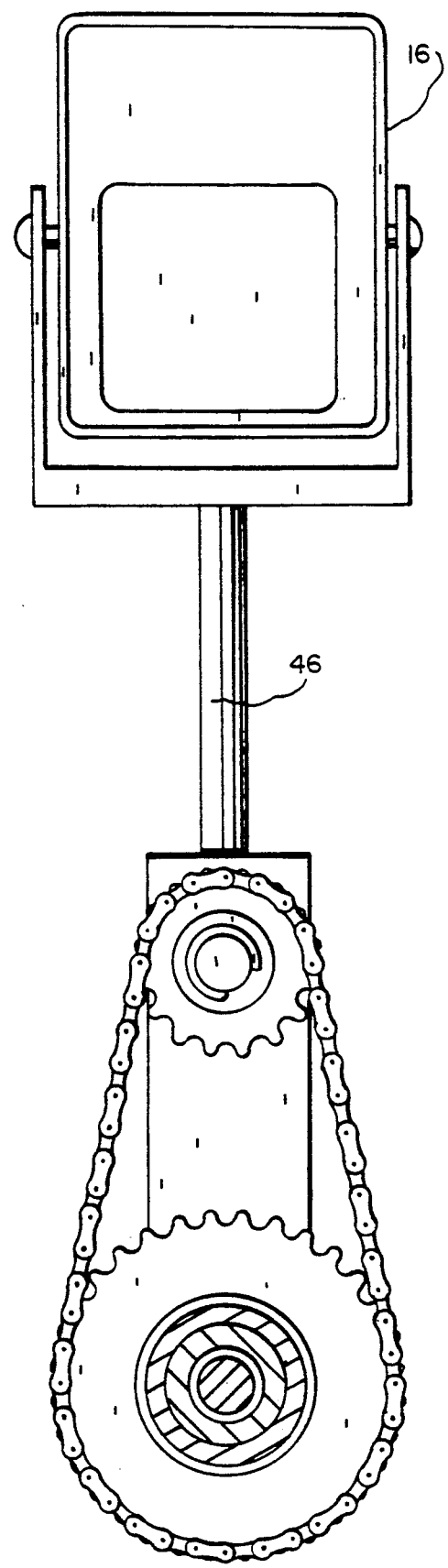
Figure 10:
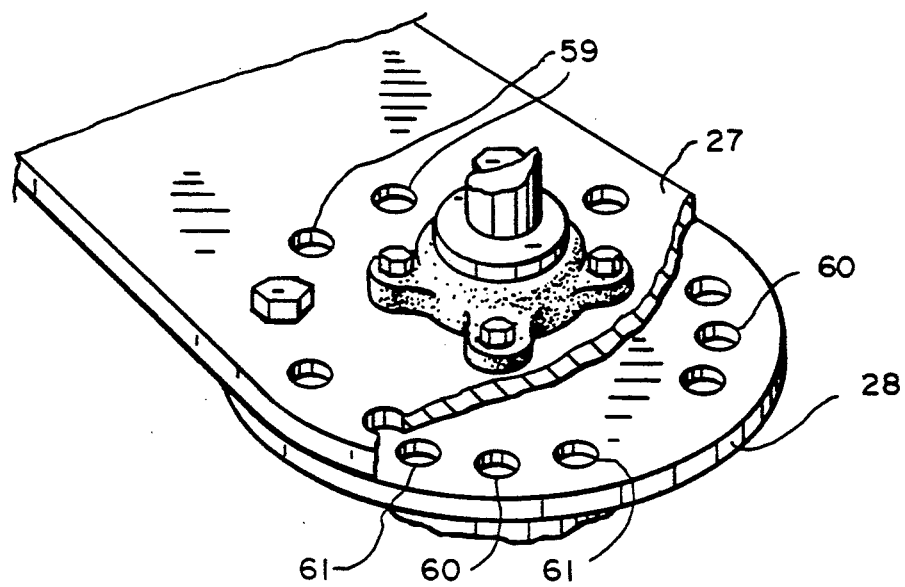
FIG. 10 a perspective view of a fragment of the mounting plates of the tare taker of FIG. 4, showing principal positioning bores and fine adjustment vernier bores, drawn to a considerably larger scale than that of FIG. 4, FIG. 11 a side elevation view of another embodiment of the beet tare taker of FIG. 1, partially cut away to show construction details, and incorporating a central arm direct drive gear, drawn to the scale of FIG. 4, and FIG. 12 a perspective view of the tare taker of FIG. 11, the mounting structure and debris shields omitted for clarity, drawn to the same scale as FIG. 3.

The illustrated and described tare taker 10 may be embodied in other forms without departing from the spirit of the invention. For example, the function of the idler gear 49 could be provided by a sprocket chain 63 or the like. (FIG. 7) Conceivably, gears 48 and 52, sprockets 20 and 22 and sprocket chains 21 and 63, could be replaced by pulley wheels and flexible drive belts, such as cog belts, respectively. Many structural and mechanical design features equivalent to those illustrated may, of course, be employed. The spacial relationships of various components may be altered. For example, the entire device 10 could be supported upwardly, rather than downwardly, from support structure 17, with bucket arm 46 then above, rather than below the gears. And, the complete device as illustrated may also be employed in simply up-ended position. Tare taker 10 could conceivably also be powered by means other than the illustrated motor 19, including by use of a suitable manual crank mechanism 62, which might be designed to engage sprocket 20. (FIG. 9)

Figure 11:
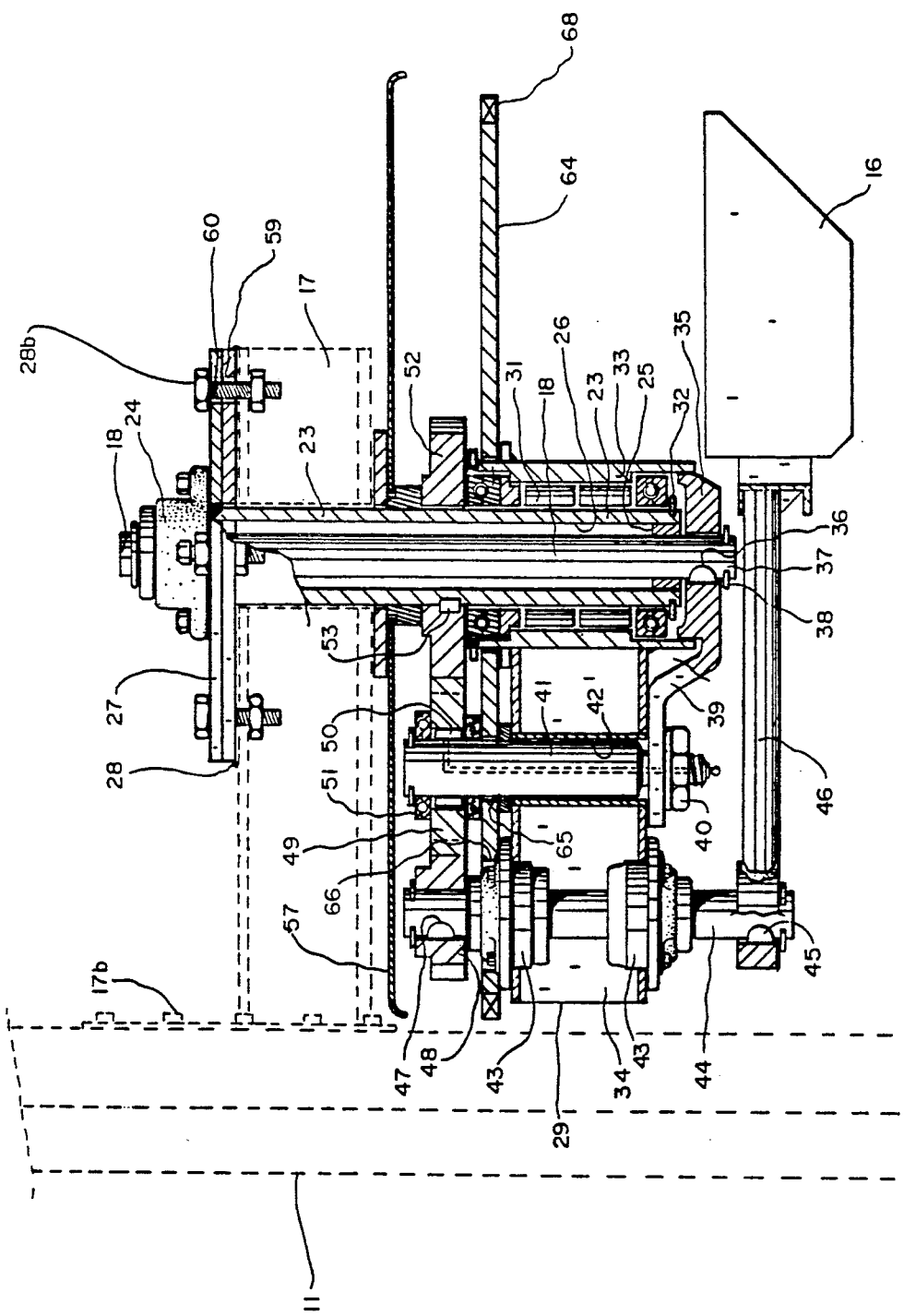
Figure 12:
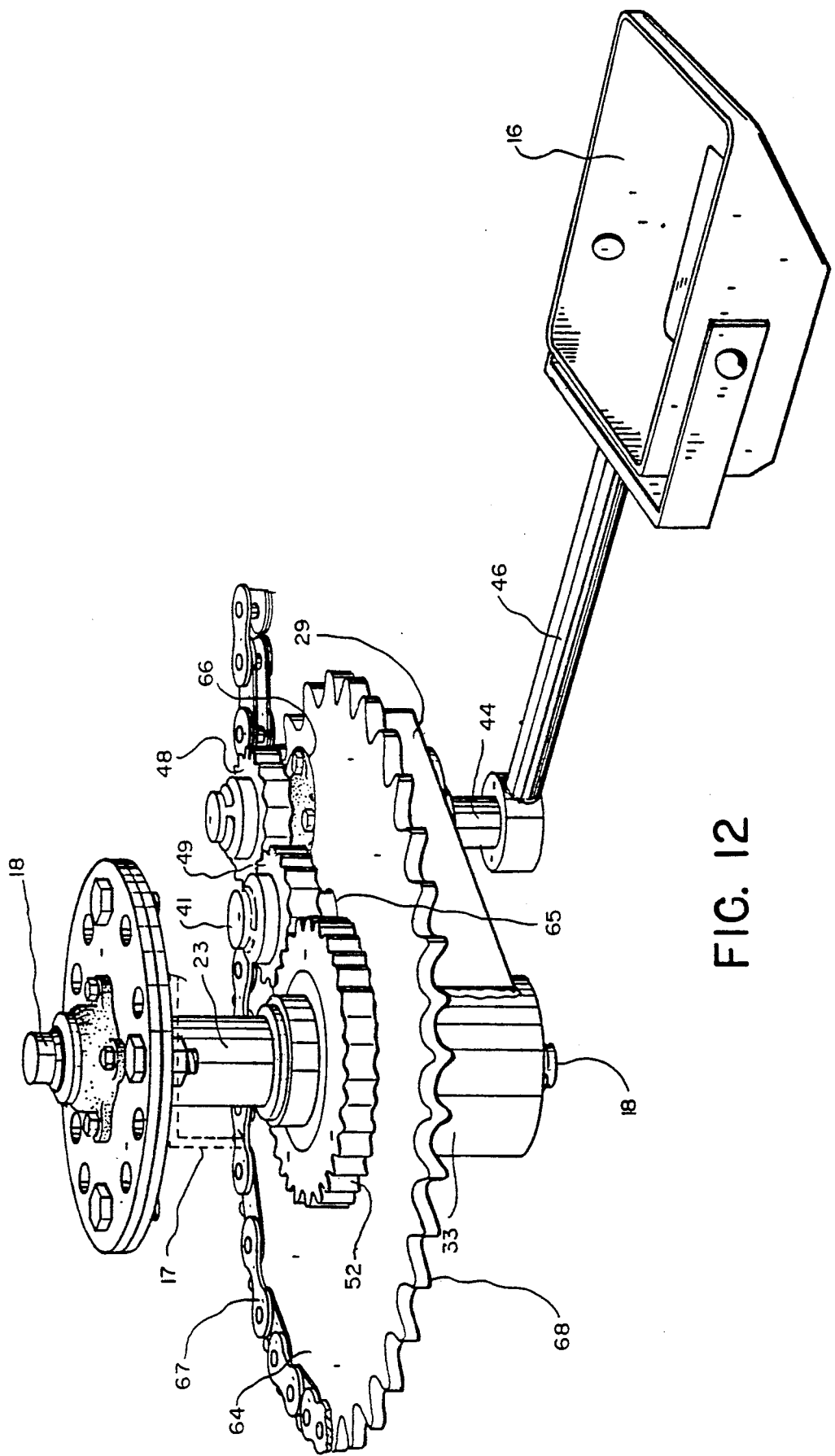

Tare taker 10 may be designed for rotation of central arm assembly 29 directly, rather than by use of the drive shaft 18. One such embodiment of tare taker 10 is illustrated in FIGS. 11 and 12, showing a central arm direct drive gear 64 mounted coaxially to drive shaft 18 and drive shaft housing tube 23. Direct drive gear 64 is mounted upon cylindrical member 33 of central arm assembly 29. Gear 64 is fixed in position upon central arm 29 engaged by vertical idler gear pinion 41 in off-center perforation 65. A clearance perforation 66 is provided to accommodate bucket arm shaft bearing 43. Gear 64 has a radius generally placing teeth 68 at or beyond the outermost end of central arm 29. This sizing assures ease of installation of sprocket drive chain 67 without interference with tare taker components. If preferred, gear 64 may be adapted to be driven by a pinion gear or the like engaging teeth 68, although the sprocket/chain drive is preferred allowing great adaptability for mounting of an associated drive motor or the like, not shown, upon conveniently adjacent structural members of the piler. Of course, gear 64 could be adapted to smaller sizes, although less advantageously. Shaft 18, although shown retained and converted into a mounting pin not utilized for driving the apparatus, could in fact be eliminated and other means of mounting central arm upon sleeve 23 employed. The use of direct drive gear 64 of course still permits the option of connection of central gear 52 and bucket arm gear 48 by means of idler gear 49 or sprocket chain 63 as desired.

The invention may be embodied in other specific forms without departing from the spirit or essential characteristics thereof. The present embodiments are therefore to be considered as illustrative and not restrictive, the scope of the invention being indicated by the appended claims rather than by the foregoing description, and all changes that come within the meaning and range of equivalency of the claims are therefore intended to be embraced therein.

What is claimed and desired to be secured by United States Letters Patent is:

1. A tare taking mechanism for carrying a tare bucket transversely through a stream of beets to obtain a sample of beets in the bucket, the mechanism comprising:

a central arm having two opposing ends and mounted to rotate about a fixed central axis perpendicular to one of the ends of said arm;

power means for rotating the central arm about the central axis, a tare bucket arm having two opposing ends and mounted to rotate about one of its ends about a bucket arm axis parallel to the central axis and through the other opposing end of the central arm;

a tare bucket attached to the other opposing end of the tare bucket arm;

means causing the bucket arm to rotate about the bucket arm axis with respect to the central arm at twice the rate of rotation of said central arm, in the opposite direction to the direction of rotation thereof; and tare mechanism support means securing the mechanism in position to cause the tare bucket to pass through the stream of beets during a desired portion of its path; wherein the central arm is secured to rotate about one of its ends about the central axis;

the tare bucket arm is fixedly secured at one of its ends outstanding from a bucket arm drive shaft mounted parallel to the central axis rotatably at the other end of the central arm;

a central arm drive gear is affixed to the central arm coaxially with the central axis;

the power means is connected to rotate the central arm drive gear; and the means causing the bucket arm to rotate with respect to the central arm comprises a central gear fixedly secured with respect to the tare mechanism support means coaxially with the central drive shaft, a bucket arm gear mounted fixedly to the bucket arm drive shaft, and drive shaft means connecting the central fixed gear and the bucket arm gear causing the latter to rotate oppositely to the direction of rotation of the central arm.

2. The tare taking mechanism of claim 1, wherein:
the central arm drive gear is sized so that a toothed perimeter thereof extends beyond the outermost end of the central arm.

3. The tare taking mechanism of claim 2, wherein:
the central arm drive gear is adapted to be driven by a sprocket chain.

4. The tare taking mechanism of claim 2, wherein:
the central arm drive gear is adapted to be driven by meshing gear means.

5. The tare taking mechanism of claim 2, wherein:
the drive means connecting the fixed central gear and the bucket arm gear is an idler gear mounted rotatably upon the central arm.

6. The tare taking mechanism of claim 2 wherein:
the drive means connecting the fixed central gear and the bucket arm gear is an endless chain.

7. The tare taking mechanism of claim 2, wherein:
the tare bucket is constructed at least partially of flexible elastic material.

8. The tare taking mechanism of claim 2, wherein:
the power means comprises an electric motor.

9. The tare taking mechanism of claim 2, wherein:
the power means comprises an electric motor with a brake.

10. The tare taking mechanism of claim 2, wherein:
the power means comprises manually operated means.

11. The tare taking mechanism of claim 2, wherein:
the tare bucket arm is mounted below the central arm, the central gear and the bucket arm gear.

12. The tare taking mechanism of claim 1, wherein:
the central gear and the bucket arm gear are mounted below the central arm.

13. The tare taking mechanism of claim 1, wherein:
the tare mechanism support means includes provisions permitting its installation in selective angular orientation with respect to the stream of beets; and provisions for selective angular orientation of the bucket arm with respect to the central arm.

* * * * *